United States Patent
Taylor et al.

(10) Patent No.: US 6,376,176 B1
(45) Date of Patent: Apr. 23, 2002

(54) METHODS OF USING A MAJOR HISTOCOMPATIBILITY COMPLEX CLASS III HAPLOTYPE TO DIAGNOSE CROHN'S DISEASE

(75) Inventors: Kent D. Taylor, Santa Paula; Jerome I. Rotter, Los Angeles; Huiying Yang, Cerritos, all of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/395,345

(22) Filed: Sep. 13, 1999

(51) Int. Cl.[7] .............................. C12Q 1/68; C12P 19/34

(52) U.S. Cl. ......................................... 435/6; 435/91.2

(58) Field of Search ........................... 435/6, 91.2, 91.1

(56) References Cited

PUBLICATIONS

Jarjour et al., "The 8.5–kb PstI Allele of the Stress Protein Gene, Hsp70–2—An Independent Risk Factor for Systemic Lupus Erythematosus in African Americans?" *Hum. Immunol.*, 45:59–63 (1996).
Owerbach and Gabbay, "The HOXD8 Locus (2q31) is Linked to Type I Diabetes—Interaction with Chromosome 6 and 11 Disease Susceptibility Genes," *Diabetes*, 44:132–136 (1995).
Singal et al., "Genetics of Rheumatoid Arthritis (RA): Two Separate Regions in the Major Histocompatibility Complex Contribute to Susceptibility to RA," *Immunol. Lett.*, 69:301–306 (1999).
Stulík et al., "The Different Expression of Proteins Recognized by Monoclonal Anti–Heat Shock Protein 70 (hsp70) Antibody in Human Colonic Diseases," 18:625–628 (1997).
GenBank Accession No: AF129756.1.
GenBank Accession No: AF134726.
GenBank Accession No: U89335.
GenBank Accession No: U89336.
Ando et al., "Triplet repeat polymorphism within the NOTCH4 gene located near the junction of the HLA class II and class III regions in narcolepsy," *Tissue Antigens* 50:646–649 (1997).
Aron et al., "Analysis of hsp70 gene polymorphism in allergic asthma," *Allergy* 54:165–170 (1999).
Brant et al., "American families with Crohn's disease have strong evidence for linkage to chromosome 16 but not chromosome 12", *Gastroenterol.* 115:1056–1061 (1998).
Curran et al., "Genetic analysis of inflammatory bowel disease in a large European cohort supports linkage to chormosomes 12 and 16,", *Gastroenterology* 115:1066–1071 (1998).
Dib et al., "A comprehensive genetic map of the human genome based on 5,264 microsatellites", *Nature* 380:152–154 (1996).

Hampe et al., "A genomewide analysis provides evidence for novel linkages in inflammatory bowel disease in a large European cohort", *Am. J. Hum. Genet.* 64:808–816 (1999).
Li et al., "Cloning, characterization, and the complete 56.8–kilobase DNA sequence of the human NOTCH4 Gene", *Genomics* 51:45–58 (1998).
Martin et al., "Recombination rates across the HLA complex: use of microsatellites as a rapid screen for recombinant chromosomes", *Human Molecular Genetics* 4:423–428 (1995).
Milner and Campbell, "Polymorphic analysis of the three MHC–linked HSP70 genes", *Immunogenetics* 36:357–362 (1992).
Moghaddam et al., "Genetic Structure of IDDM1: Two Separate Regions in the Major Histocompatibility Complex Contribute to Susceptibility or Protection," *Diabetes* 47:263–269 (1998).
Pociot et al., "Polymorphic analysis of the human MHC–linked heat shock protein 70 (HSP70–2) and HSP70–Hom Genes in insulin–dependent diabetes mellitus (IDDM)," *Scand. J. Immunol.* 38:491–495 (1993).
Roth et al., "Familial empiric risk estimates of inflammatory bowel disease in Ashkenazi Jews," *Gastroenterology* 96:1016–1020 (1989).
Roth et al., "Geographic origins of Jewish patients with inflammatory bowel disease," *Gastroenterology* 97:900–904 (1989).
Rozen et al., "Crohn's disease in the Jewish population of Tel–Aviv–Yafo. Epidemiologic and clinical aspects," *Gastroenterology* 76:25–30 (1979).
Silverberg et al., "The HLA DRBL 0103 Allele is Associated with Crohn's Disease (CD) in a Toronto Inflammatory Bowel Disease (IBD) Population," *Gastroenterology* 116:G3559 AGA Abstracts (1999).
Silverberg et al., "Evidence for Linkage Between Crohn's Disease (CD) and a Locus Near the Major Histocompatibility Complex (MHC) on Chromosome 6 in a Canadian Inflammatory Bowel Disease (IBD) Population," *Gastroenterology* 116:G3560 AGA Abstracts (1999).
Singal et al., "D6S273 Microsatellite Polymorphism and Susceptibility to Rheumatoid Arthritis," *Tissue Antigens* 52:353–358 (1998).

(List continued on next page.)

*Primary Examiner*—W. Gary Jones
*Assistant Examiner*—Jehanne Souaya
(74) *Attorney, Agent, or Firm*—Campbell & Flores LLP

(57) ABSTRACT

The present invention provides a method of diagnosing or predicting susceptibility to an autoimmune disease in an individual by determining the presence or absence in the individual of a 2-2-4 haplotype at the Notch4, HSP70-HOM and D6S273 loci, where the presence of the haplotype diagnoses or predicts susceptibility to the autoimmune disease. The methods of the invention can be particularly useful for diagnosing or predicting susceptibility to Crohn's disease, rheumatoid arthritis or type I diabetes mellitus. In a preferred embodiment, a method of the invention is used to diagnose or predict susceptibility to Crohn's disease in an individual of Ashkenazi Jewish ethnicity.

8 Claims, 5 Drawing Sheets

OTHER PUBLICATIONS

Sugaya et al., "Gene organization of human NOTCH4 and (CTG)n polymorphism in this human counterpart gene of mouse proto–oncogene Int3," *Gene* 189:235–244 (1997).

Sugaya et al., "Three genes in the human MHC class III region near the junction with the class II: gene for receptor of advanced glycosylation end products, PBX2 homeobox gene and a notch homolog, human counterpart of mouse mammary tumor gene int–3," *Genomics* 23:408–419 (1994).

Sullivan et al., "Prevalence of a mutation causing C2 deficiency in systemic lupus erythematosus," *The Journal of Rheumatology* 21:1128–1133 (1994).

Trachtenberg et al., "Rare HLA DR–DQ Haplotypes Associated with Inflammatory Bowel Disease," *Human Immunol.* 55(supp. 1):59 (1997).

Trowsdale et al., "Map of the human MHC," *Immunol. Today* 12:443–446 (1991).

Yamamoto–Furusho et al., "Complotype SC30 is associated with susceptibility to develop ulcerative colitis in Mexicans," *J. Clin. Gastroenterology* 27(2):178–180 (1998).

Yang and Rotter in Kirschner and Shorter (Eds.), *Inflammatory Bowel Disease* Baltimore: Williams and Wilkins, p. 301–331 (1995).

Yang et al., "Familial empirical risks for inflammatory bowel disease: differences between Jews and non–Jews," *Gut* 34:517–524 (1993).

Yang et al., "Linkage of Crohn's disease to the major histocompatibility complex region is detected by multiple non–parametric analyses," *Gut* 44:519–526 (1999).

| Marker | Type | Location | Landmarks | Primer | SEQ. ID NO. | Direction | Enzyme | Reference |
|---|---|---|---|---|---|---|---|---|
| Taposin | ms | 0.10 | | HEC CTG TAA TCC CAG CTA CTC AAT CG | 1 | forward | | This work based on GenBank Z97183 |
| | | | | GGG AGA CTT AAA CAG CAG AAA TGT | 2 | reverse | | |
| HKE 6 | ms | 0.22 | | TET TCG GGA TCA TTT CAG TAA TCT | 3 | forward | | Kikuti et al., *Genomics* 42:422-435 (1997). This work based on GenBank D84401 |
| | | | | GGG ATC CGC TGT AAC TCT | 4 | reverse | | |
| | | 0.35 | HLA-DPB1 | | | | | |
| Tap1 | ms | 0.6 | | HEX GGA CAA TAT TTT GCT CCT GAG G | 5 | forward | | GDB ID G00-250-903; Carrington & Dean, *Human Molecular Genetics* 3:218 (1994) |
| | | | | GCT TTG ATC TCC CCC CTC | 6 | reverse | | |
| | | 0.75 | HLA-DQB1 | | | | | |
| | | 0.83 | HLA-DRB1 | | | | | |
| HLA-DRA | snp | 1.0 | | GAG CTC GGG AGT GAG GCA GAA CAG | 7 | forward | DdeI | Eliaou et al., *Nucleic Acids Res.* 18:7195 (1990) |
| | | | | TGA GGT GTG TTC ATT AGT CAA CTC | 8 | reverse | | |
| Notch4 | ms | 1.2 | | FAM CGT CTC TAT TTG GGC AGT GAG | 9 | forward | | Sugaya et al., *Gene* 189:235-244 (1997) |
| | | | | GGC CGA GGA GGA AGA AGA | 10 | reverse | | |
| HSP-HOM | snp | 1.6 | | CCG GAT CCC ATA GGC CTC AGA GAA CC | 11 | forward | NcoI | Milner & Campbell, *Immunogenetics* 36:357-362 (1992) |
| | | | | GTA ACT TAG ATT CAG GTC TGG | 12 | reverse | | |
| D6S273 | ms | 1.7 | | FAM ACC AAA CTT CAA ATT TTC GG | 13 | forward | | GDB id G00-133-162; AFM142xh6; Gyapay et al., *Nature Genetics* 7:246-339 (1994) |
| | | | | GCA ACT TTT CTG TCA ATC CA | 14 | reverse | | |
| Bat2 | ms | 1.8 | | HEX GGA GCT AAA AGT TCT AAC TC | 15 | forward | | This work based on GenBank Z15025 |
| | | | | TGT CTC AAA ATA TTA ATG TG | 16 | reverse | | |

Figure 1A

| Marker | Type | Location | Landmarks | Primer | SEQ. ID NO. | Direction | Enzyme | Reference |
|---|---|---|---|---|---|---|---|---|
| IST1 | snp | 1.84 | | TAG TAA TTT GTT GGG TGA ATG ACA | 17 | forward | PvuII | DeBaey et al., *Human Immunol.* 42:9-14 (1994). This work based on GenBank U00921 |
| | | | | CAC ACT GCC ACT CCT CAG AT | 18 | reverse | | |
| TNFd | ms | 1.84 | | TET CAT AGT GGG ACT CTG TCT CCA AAG | 19 | forward | | Nedospasov et al., *J.Immunol.* 147:1053-1059 (1991); Udalova et al., *Genomics* 16:180-186 (1993) |
| | | | | AGA TCC TTC CCT GTG AGT TCT GCT | 20 | reverse | | |
| TNFe | ms | 1.84 | | TET GTG CCT GGT TCT GGA GCC TCT C | 21 | forward | | Nedospasov et al., *supra*, (1991); Udalova et al., *supra*, (1993) |
| | | | | TGA GAC AGA GGA TAG GAG AGA CAG | 22 | reverse | | |
| | | | TNFα | | | | | |
| TNFc | ms | 1.86 | TNFβ | HEX GGT TTC TCT GAC TGC ATC TTG TCC | 23 | forward | | Nedospasov et al., *supra*, (1991); Udalova et al., *supra*, (1993) |
| | | | | TCA TGG GGA GAA CCT GCAGAG AA | 24 | reverse | | |
| TNFa | ms | 1.86 | | HEX CCT CTC TCC CCT GCA ACA CAC A | 25 | forward | | Nedospasov et al., *supra*, (1991); Udalova et al., *supra*, (1993) |
| | | | | GCC TCT AGA TTT CAT CCA GCC ACA | 26 | reverse | | |
| TNFb | ms | 1.86 | | HEX GTG TGT GTT GCA GGG GAG AGA G | 27 | forward | | Nedospasov et al., *supra*, (1991); Udalova et al., *supra*, (1993) |
| | | | | GCA CTC CAG CCT AGG CCA CAG A | 28 | reverse | | |
| MICA | ms | 2.1 | | TET ACA ATG GAC ACT TGG GTT ACT | 29 | forward | | Mizuki et al., *Diabetes* 47:263-269 (1997) |
| | | | | AAT GAG ATG CCA CCT GAA A | 30 | reverse | | |
| | | 2.1 | HLA-B | | | | | |
| | | 2.2 | HLA-C | | | | | |
| C2-4-4 | ms | 2.4 | | TET TTA TCT ACT TAT AGT CTA CGG | 31 | forward | | Tamiya et al., *Tissue Antigens* 51:337-346 (1998) |
| | | | | GGC TTG ACT TGA AAC TCA GAG ACC | 32 | reverse | | |

Figure 1B

| Marker | Type | Location | Landmarks | Primer | SEQ. ID NO. | Direction | Enzyme | Reference |
|---|---|---|---|---|---|---|---|---|
| TUBB | ms | 2.5-2.7 | | FAM GAT CGC TCA CCA GCA CAC TGG CTA T | 33 | forward | | Zuliani & Hobbs, *Am J Hum Genet.* 46:963-969 (1990); This work based on GenBank X00734 |
| | | | | CTG GGC AAC AGA GCG AGC TCC GTC T | 34 | reverse | | |
| C3-2-11 | ms | 2.9 | | FAM TCC TTA CAG CAG AGA TAT GTG G | 35 | forward | | Tamiya et al., *supra*, (1998) |
| | | | | AGA TGG CAT TTG GAG AGT GCA G | 36 | reverse | | |
| | | 3.4 | HLA-A | | | | | |
| D6S510 | ms | 3.4 | | FAM CAA CAC ACT GAT TTC CAT AGC | 37 | forward | | GDB id G00-249-443; Gondon et al., *Human Molecular Genetics* 3:1210 (1994) |
| | | | | AAT GGG CTA CTA CTT CAC ACC | 38 | reverse | | |
| MOG11 | ms | 3.9 | | HEX GAA ATG TGA GAA TAA AGG AGA | 39 | forward | | Roth et al., *Human Immunol.* 43:276-282 (1995) |
| | | | | GAT AAA GGG GAA CTA CTA CA | 40 | reverse | | |

Figure 1C

Association of MHC markers in the Jewish case-control panel

| Marker | Number of alleles | P | Allele | Allele Frequency | |
|---|---|---|---|---|---|
| | | | | CD | Control |
| Tapasin | 12 | 0.88 | | | |
| HKE6 | 9 | 0.90 | | | |
| Tap1 | 9 | 0.44 | | | |
| HLA-DRA | 2 | 0.021 | | | |
| Notch4 | 7 | 0.011 | 2 | 35% | 25% |
| HSP-HOM | 2 | 0.12 | | | |
| D6S273 | 7 | 0.84 | | | |
| Bat2 | 12 | 0.12 | | | |
| LST1 | 2 | 0.30 | | | |
| TNFd | 6 | 0.34 | | | |
| TNFe | 3 | 0.23 | | | |
| TNFc | 2 | 0.33 | | | |
| TNFa | 13 | 0.37 | | | |
| TNFb | 5 | 0.78 | | | |
| MICA | 11 | 0.87 | | | |
| C2-4-4 | 11 | 0.70 | | | |
| TUBB | 5 | 0.014 | 4 | 5% | 37% |
| C3-2-11 | 20 | 0.92 | | | |
| D6S510 | 9 | 0.79 | | | |
| MOG11 | 10 | 0.31 | | | |

Figure 2

| HLA-DRA | Notch4 | Hsp-HOM | D6S273 | TNF | Bat2 | LST1 | p | Transmitted | Not Transmitted | Odds Ratio (95%CI) |
|---|---|---|---|---|---|---|---|---|---|---|
| 2 | | | | | | | 0.49 | 19 | 15 | 1.27 (0.58, 2.79) |
| | 2 | | | | | | 0.011 | 31 | 15 | 2.07 (4.03, 4.24) |
| | | 2 | | | | | 0.050 | 15 | 6 | 2.5 (0.83, 8.41) |
| | | 2 | 4 | | | | 0.0044 | 29 | 11 | 2.64 (1.2, 6.05) |
| | | | 4 | | 5 | | 0.22 | 32 | 23 | 1.39 (0.76, 2.56) |
| | | | | | 5 | 1 | 0.025 | 5 | 0 | 10 (0.5, 58) |
| | | | | | | 1 | 0.029 | 13 | 4 | 43.25 (0.88, 15.2) |
| 2 | 2 | 2 | 4 | | 5 | | 0.050 | 15 | 6 | 2.5 (0.83, 8.41) |
| | 2 | 2 | 4 | | 5 | | 0.00097 | 16 | 2 | 8.0 (1.55, 100) |
| | | 2 | 4 | | | | 0.025 | 5 | 0 | 10.0 (0.5, 58) |
| | | | 4 | | | | 0.025 | 5 | 0 | 10.0 (0.5, 58) |

Class II — HLA-DRB1 | Class III (Hsp-HOM, D6S273, TNF, Bat2, LST1) | Class I — HLA-B, HLA-A

Figure 3

METHODS OF USING A MAJOR HISTOCOMPATIBILITY COMPLEX CLASS III HAPLOTYPE TO DIAGNOSE CROHN'S DISEASE

This work was supported by grant DK46763 awarded by NIDDK. The United States government has certain rights in this invention.

BACKGROUND OF THE INVENTION

1. Field of the Invention

The invention relates generally to the fields of autoimmunity and inflammatory bowel disease and more specifically to genetic methods for diagnosing Crohn's disease and other autoimmune diseases.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

A battery of laboratory, radiological, and endoscopic evaluations are typically combined to derive a diagnosis of IBD and to assess the extent and severity of the disease. Nevertheless, differentiating Crohn's disease from ulcerative colitis, as well as other types of inflammatory conditions of the bowel, such as irritable bowel syndrome, infectious diarrhea, rectal bleeding, radiation colitis and the like, is difficult because the mucosa of the small and large intestines reacts in a similar way to a large number of different insults. Furthermore, the extensive and often protracted clinical testing required to diagnose CD delays accurate diagnosis and treatment and involves invasive procedures such as endoscopy.

To date, a reliable genetic test for Crohn's disease, which would be highly prized as a non-invasive method for the early diagnosis of Crohn's disease, is not available. Such a test, based on identifying genetic markers that are associated with a predisposing mutation to an autoimmune disease such as Crohn's disease, would obviate invasive clinical procedures. Such a genetic assay also would be useful in methods of predicting susceptibility to Crohn's disease in asymptomatic individuals, making prophylactic therapy possible. Unfortunately, genetic markers closely associated with Crohn's disease have yet to be identified. The present invention satisfies this need and provides related advantages as well.

SUMMARY OF THE INVENTION

The present invention provides a method of diagnosing or predicting susceptibility to an autoimmune disease in an individual by determining the presence or absence in the individual of a 2-2-4 haplotype at the Notch4, HSP70-HOM and D6S273 loci, where the presence of the haplotype diagnoses or predicts susceptibility to the autoimmune disease. The methods of the invention can be particularly useful for diagnosing or predicting susceptibility to Crohn's disease, rheumatoid arthritis and Type I diabetes mellitus. In a preferred embodiment, the methods of the invention are used to diagnose or predict susceptibility to Crohn's disease in an individual of Ashkenazi Jewish ethnicity.

In one embodiment, the invention provides a method of diagnosing or predicting susceptibility to an autoimmune disease by determining the presence or absence of the 2-2-4 haplotype using enzymatic amplification of nucleic acid from the individual. Subsequent to such enzymatic amplification, the presence or absence of the 2-2-4 haplotype can be determined by electrophoresis such as automated capillary electrophoresis. In another embodiment, the presence or absence of the 2-2-4 haplotype can be determined following enzymatic amplification using restriction fragment length polymorphism analysis. In another embodiment, following enzymatic amplification, the presence or absence of the 2-2-4 haplotype is determined using sequence analysis.

In one embodiment, the presence or absence of the 2-2-4 haplotype can be determined by obtaining material including nucleic acid including Notch4, HSP70-HOM and D6S273 loci from the individual, enzymatically amplifying the nucleic acid to produce a first amplified fragment containing the Notch4 locus, enzymatically amplifying the nucleic acid to produce a second amplified fragment containing the HSP70-HOM locus, and enzymatically amplifying the nucleic acid to produce a third amplified fragment containing the D6S273 locus. Additionally, the presence or absence of the 2-2-4 haplotype can be determined by electrophoresing the first amplified fragment to determine whether a Notch4 allele 2 is present, electrophoresing the second amplified fragment to determine whether a HSP70-HOM allele 2 fragment is present and electrophoresing the third amplified fragment to determine whether a D6S273 allele 4 is present. The presence of the Notch4 allele 2, the HSP70-HOM allele 2 and the D6S273 allele 4 indicates that the 2-2-4 haplotype is present. In one embodiment, the second amplified fragment is restricted with Nco I or an isoschizomer thereof.

The invention also provides a method of diagnosing or predicting susceptibility to an autoimmune disease in an individual by determining the presence or absence in the individual of a disease-associated haplotype which is associated with a 2-2-4 haplotype at the Notch4, HSP70-HOM and D6S273 loci, where the presence of the disease-associated haplotype is diagnostic of or predictive of susceptibility to the autoimmune disease. In one embodiment, the disease-associated haplotype is associated with the autoimmune disease with an odds ratio of at least 5 and a lower 95% confidence limit of greater than 1. The methods of the invention are useful for diagnosing an autoimmune disease such as Crohn's disease, rheumatoid arthritis or diabetes and can be particularly useful for diagnosing Crohn's disease in an individual of Ashkenazi Jewish ethnicity.

The present invention also provides methods for diagnosing or predicting susceptibility to an autoimmune disease in an individual by determining the presence or absence of a disease-associated allele associated with the 2-2-4 haplotype at the Notch4, HSP70-HOM and D6S273 loci, where the presence of the disease-associated allele is diagnostic of or predictive of susceptibility to the autoimmune disease. In one embodiment, the disease-associated allele is associated with the autoimmune disease with an odds ratio of at least 5 and a lower 95% confidence limit of greater than 1.

BRIEF DESCRIPTION OF THE DRAWINGS

FIG. 1 shows an analysis of haplotype association to Crohn's disease (CD) using the transmission disequilibrium test. Top. Illustration of the relative positions of the markers analyzed with respect to the standard major histocompatibility complex (MHC) map. Below each marker is the allele or allelic combination with the nominal p value and odds ratio with 95% confidence interval for the transmission distortion of the individual haplotype to affecteds calculated using GeneHunter 2.0. "ms" indicates microsatellite; "snp" indicates single nucleotide polymorphism.

FIG. 2 shows the association of markers with Crohn's disease in the Jewish case-control panel.

FIG. 3 shows the analysis of haplotype association with Crohn's disease using the transmission disequilibrium test. Top: Relative positions of several markers analyzed are shown with respect to a standard map of the major histocompatibility complex. Bottom: The number of haplotypes transmitted and not transmitted to affected patients with Crohn's disease is shown.

DETAILED DESCRIPTION OF THE INVENTION

Despite evidence of a genetic component to Crohn's disease, genetic markers that can be responsible for disease susceptibility or that can be reliably used as diagnostic markers for Crohn's disease have not been identified. The present invention is directed to the exciting discovery of a three marker haplotype within the major histocompatibility complex (MHC or HLA) class III region that is closely associated with Crohn's disease in individuals of Ashkenazi Jewish ethnicity.

As disclosed herein, a linkage disequilibrium approach was used to identify a strong genetic association with Crohn's disease in individuals of Ashkenazi Jewish ethnicity. A case control panel made up of 108 individuals with CD and 69 controls, and a family panel made up of 56 families with at least one member affected with Crohn's disease, were analyzed at 21 MHC markers (see Example 1 and FIG. 1). As disclosed herein, Notch4 allele 2 was associated with Crohn's disease in both the case control and family panels, with 31 transmitted to affecteds (T) and 15 not transmitted (NT; see FIG. 3; p=0.011). As further disclosed herein, a 2-2 haplotype formed with the adjacent single nucleotide polymorphism (SNP) marker, HSP70-HOM, yielded a stronger association with Crohn's disease in this population, as indicated by 29 transmitted to affecteds and 11 not transmitted (p=0.0044). As further shown in FIG. 3, a 2-2-4 Notch 4, HSP70-HOM and D6S273 haplotype displayed an extremely strong association with Crohn's disease, as indicated by 16 transmitted to affecteds and two non-transmitted (p=0.00097). Thus, this MHC class III 2-2-4 haplotype is strongly associated with Crohn's disease and can be used to diagnose Crohn's disease or related autoimmune diseases, and to predict susceptibility to disease in high risk individuals.

Thus, the present invention provides methods for diagnosing or predicting susceptibility to an autoimmune disease in an individual by determining the presence or absence in the individual of a 2-2-4 haplotype at the Notch4, HSP70-HOM and D6S273 loci, where the presence of the 2-2-4 haplotype is diagnostic of or predictive of susceptibility to the autoimmune disease. The methods of the invention are advantageous in that they are noninvasive, conveniently practiced, for example, with a blood sample from an individual. The methods of the invention also are advantageous in regard to the confidence in results that they provide. In testing for Crohn's disease, for example, the present invention is based on the strongest association seen to date between any genetic marker or haplotype and CD. Thus, the present invention can be used to quickly, easily and reliably diagnose or predict susceptibility to an autoimmune disease such as Crohn's disease.

The present invention relies on genetic markers found in the MHC, which includes three distinct regions: classes I, II and III. See FIG. 3 for an illustration of the standard MHC map (Trowsdale et al., *Immunol. Today* 12:443–446 (1991)). In particular, the invention relies, in part, on a polymorphism in Notch4, a member of the Notch gene family, which is positioned near the centromeric end of the class III locus (Sugaya et al., *Genomics* 23: 408–419 (1994)). Notch4 was cloned and characterized as described in Li et al., *Genomics* 51: 45–58 (1998), and the sequence of the Notch4 gene can be found in GenBank as accession numbers U89335 and U89336, which are incorporated by reference herein. A polymorphism in a $(CTG)_n$ trinucleotide repeat is present in the first exon of the Notch4 gene, located between nucleotides 24,000 and 24,026 of accession number U89335, in the region encoding the Notch4 signal peptide. Analysis of individual variable number tandem repeats (VNTRs) has revealed that there are 7 alleles, with the longest repeat unit $(CTG)_{12}$, and the shortest $(CTG)_6$ (Sugaya et al., *Gene* 189:235–244 (1997)).

One skilled in the art recognizes that a particular polymorphic allele can be conveniently defined in comparison to a Centre d'Etude du Polymorphisme Humain (CEPH) reference individual such as the individual designated 1347-02 (Dib et al., *Nature* 380:152–154 (1996)), using commercially available reference DNA obtained, for example, from PE Biosystems (Foster City, Calif.). As used herein, the term "Notch4 allele 2" means the smaller of the two Notch4 alleles present in CEPH reference individual 1347-02. Using primers 5'-FAM-CGTCTCTATTTGGGCAGTGAG-3' (SEQ ID NO: 9) and 5'-GGCCGAGGAGGAAGAAGA-3' (SEQ ID NO: 10), 325 and 328 bp fragments are generated from CEPH reference individual 1347-02. As disclosed herein, the presence of allele 2 can be conveniently detected, for example, by capillary electrophoresis of an amplified fragment prepared with primers SEQ ID NOS: 9 and 10 as a 325 basepair (bp) fragment (see FIG. 1).

The invention also relies, in part, on a biallelic polymorphism in HSP70-HOM (Milner and Campbell, *Immunogenetics* 36: 357–362 (1992)). The heat shock proteins (HSP70) are encoded by a multigene family in humans and implicated in immune response; three genes encoding members of the HSP70 family are located in the class III region of the MHC: HSP70-1, HSP70-2 and HSP70-HOM. The complete sequence of HSP70-HOM, which encodes a protein with 90% sequence identity with HSP70-1 (Milner and Campbell, supra, 1992), can be found in GenBank accession number AF134726, which is incorporated by reference herein. HSP70-HOM contains a polymorphism at nucleotide 2437; the "T" to "C" nucleotide transition corresponds to a methionine to threonine substitution at amino acid 493 (M493T; Milner and Campbell, supra, 1992). As exemplified herein, allele 2 can be conveniently distinguished from allele 1 by PCR amplification of total genomic DNA with primers 5'-CCGGATCCCATAGGCCTCAGAGAACC-3' (SEQ ID NO: 11) and 5'-GTAACTTAGATTCAGGTCTGG-3' (SEQ ID NO: 12)

and subsequent digestion of the amplified fragment with restriction enzyme Nco I. This enzyme restricts the "2" allele ("T" at nucleotide 2437) to produce two fragments of about 750 bp and 350 bp, while the "1" allele ("C" at nucleotide 2437) remains an uncleaved 1.1 kb fragment (see Example II). As used herein, the term "HSP70-HOM allele 2" means an HSP70-HOM allele having a "T" at nucleotide position 2437 and capable of being cleaved under the appropriate conditions by restriction enzyme Nco I.

The 2-2-4 haplotype also involves the D6S273 microsatellite polymorphism available as nucleotides 34,073 to 34,114 of GenBank accession number. AF129756.1, which is incorporated by reference herein. There are seven D6S273 alleles, with standard nomenclature designating the 140 bp fragment as allele 1; the 138 bp fragment as allele 2; the 136 bp fragment as allele 3; the 134 bp fragment as allele 4; the 132 bp fragment as allele 5; the 130 bp fragment as allele 6 and the 128 bp fragment as allele 7. Typing of CEPH reference individual 1347-02 indicates that this individual has alleles 3 and 5 (Martin et al., *Human Molecular Genetics* 4:423–428 (1995); GBD ID:G00-574-167). As used herein, the term "D6S273 allele" means an allele intermediate in size between the two D6S273 alleles of CEPH reference individual 1347-02. As exemplified herein (see Example II), allele 4 can be conveniently detected as a fragment intermediate in size between the two D6S273 alleles of CEPH reference individual 1347-02 upon amplification with primers 5'-FAM-ACCAAACTTCAAATTTTCGG-3' (SEQ ID NO: 13) and 5'-GCAACTTTTCTGTCAATCCA-3' (SEQ ID NO: 14; see, also, FIG. 1). The D6S273 allele 4 fragment can migrate with an apparent size of 133 bp, although it corresponds to the 134 bp fragment reported in Martin et al., supra, 1995.

The class III microsatellite marker D6S273 has previously been associated in type I diabetic subjects with the highest risk class II HLA-DQ alleles (Moghaddam et al., *Diabetes* 47:263–269 (1998)) and in rheumatoid arthritis subjects with the high risk class II HLA-DRB1 QKRAA/QRRAA shared epitope (Singal et al., *Tissue Antigens* 52:353–358 (1998)). However, the D6S273 marker has not previously been associated with Crohn's disease, nor has a haplotype made up of Notch 4 allele 2, HSP70-HOM allele 2 and D6S273 allele 4 been identified.

As used herein, the term "2-2-4 haplotype" means a haplotype composed of Notch 4 allele 2, HSP70-HOM allele 2 and D6S273 allele 4.

As used herein, the term "individual" means an animal, such as a human or other mammal, capable of having an autoimmune disease. An individual can have one or more symptoms of an autoimmune disease or can be asymptomatic. The methods of the invention can be particularly useful for diagnosing an autoimmune disease in an individual with one or more symptoms, or for predicting susceptibility to an autoimmune disease in an individual, such as an individual at increased risk for having the disease, before any pathological characteristics are manifest.

The methods of the present invention are useful for diagnosing or predicting susceptibility to a variety of autoimmune diseases including, for example, Crohn's disease, rheumatoid arthritis and diabetes. As used herein, the term "autoimmune disease" means a disease resulting from an immune response against a self tissue or tissue component, including both self antibody responses and cell-mediated responses. The term autoimmune disease, as used herein, encompasses organ-specific autoimmune diseases, in which an autoimmune response is directed against a single tissue, such as Crohn's disease and ulcerative colitis, Type I diabetes mellitus, myasthenia gravis, vitiligo, Graves' disease, Hashimoto's disease, Addison's disease and autoimmune gastritis and autoimmune hepatitis. The term autoimmune disease also encompasses non-organ specific autoimmune diseases, in which an autoimmune response is directed against a component present in several or many organs throughout the body. Such autoimmune diseases include, for example, rheumatoid disease, systemic lupus erythematosus, progressive systemic sclerosis and variants, polymyositis and dermatomyositis. Additional autoimmune diseases include pernicious anemia including some of autoimmune gastritis, primary biliary cirrhosis, autoimmune thrombocytopenia, Sjögren's syndrome, multiple sclerosis and psoriasis. One skilled in the art understands that the methods of the invention can be applied to these or other autoimmune diseases, as desired.

The methods of the present invention are particularly useful for diagnosing or predicting susceptibility to Crohn's disease, or regional enteritis, which is a disease of chronic inflammation that can involve any part of the gastrointestinal tract. Commonly the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also can include extra-intestinal complications such as inflammation of the eye, joints and skin; liver disease; kidney stones or amyloidosis. CD is also associated with an increased risk of intestinal cancer.

Several features are characteristic of the pathology of Crohn's disease. The inflammation associated with CD, known as transmural inflammation, involves all layers of the bowel wall. Thickening and edema, for example, typically appear throughout the bowel wall, with fibrosis also present in long-standing disease. The inflammation characteristic of CD also is discontinuous with segments of inflamed tissue, known as "skip lesions," separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. About half of Crohn's disease cases display the typical discrete granulomas, while others show a diffuse granulomatous reaction or nonspecific transmural inflammation. As a result, the presence of discrete granulomas is indicative of CD, although the absence granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J.B. Lippincott Company (1994)).

The 2-2-4 haplotype at the Notch4, HSP70-HOM, and D6S273 loci can be particularly useful in diagnosing or predicting susceptibility to an autoimmune disease in an individual who is an Ashkenazi Jew. In a preferred embodiment, the 2-2-4 haplotype is used in an individual who is an Ashkenazi Jew to diagnose or predict susceptibility to Crohn's disease, which is significantly more common (2 to 8 fold higher) in Ashkenazi Jews than in non-Jewish Caucasians (Brant et al., *Gastroenterol.* 115:1056–1061 (1998)). Among persons of Jewish ethnicity, American or European Ashkenazi Jews have a 2 to 4 fold increased risk of having this inflammatory bowel disease compared with Sephardic or Oriental Jews (Yang and Rotter in Kirschner and Shorter (Eds.), *Inflammatory Bowel Disease* Baltimore: Williams and Wilkins, p. 301–331 (1995); Rozen et al., *Gastroenterol.* 76:25–30 (1979)); Ashkenazi Jews of middle European origin also have an excess risk compared with those of Polish or Russian origin (Roth et al., *Gastroenterol.* 97:900–904 (1989)). The empiric risk for a first degree relative of a proband with CD is 7.8% for Jews compared with 5.2% for non-Jews (p=0.005; Yang et al., *Gut* 34:517–524 (1993)). Thus, the disclosed method based on the 2-2-4 haplotype can be particularly valuable for diagnosing or predicting susceptibility to Crohn's disease in this high-risk group, and further can be useful for diagnosing or predicting susceptibility to other autoimmune diseases such as rheumatoid arthritis or Type I diabetes in an individual of Ashkenazi Jewish ethnicity.

As used herein, the term "Ashkenazi Jew" refers to an individual of Jewish ethnicity who is a descendant of a Jew originating from central or eastern Europe. The term "Ashkenazi Jew" is in distinction to a Sepharadi, who is a descendant of a Jew expelled from Spain, or an Oriental Jew, who is a descendant of a Babylonian Jew. Ashkenazi Jewish identity can be established, for example, as described in Roth et al., *Gastroenterol.* 96:1016–1020 (1989); Roth et al., supra, 1989; and Yang et al., supra, 1993.

The methods of the invention also can be particularly useful for diagnosing or predicting susceptibility to rheumatoid arthritis. Rheumatoid arthritis is a chronic systemic disease primarily of the joints, usually polyarticular, marked by inflammatory changes in the synovial membranes and articular structures and by muscle atrophy and rarefaction of the bones.

The disclosed 2-2-4 haplotype also can be useful for diagnosing or predicting susceptibility to Type I diabetes according to a method of the invention. Type I diabetes, also known as insulin-dependent diabetes mellitus (IDDM), usually appears in childhood but can appear at any age and is due to a deficiency of insulin, which may be caused by inadequate proinsulin production by the pancreas, by an accelerated destruction of insulin, or by insulin antagonists and inhibitors. Type I diabetes is typically characterized by polydipsia, polyuria, increased appetite, weight loss, low plasma insulin levels, and episodic ketoacidosis.

In one embodiment, the invention provides a method of diagnosing or predicting susceptibility to an autoimmune disease by determining the presence or absence of the 2-2-4 haplotype using enzymatic amplification of nucleic acid from the individual. Subsequent to such enzymatic amplification, the presence or absence of the 2-2-4 haplotype can be determined by electrophoretic analysis. In another embodiment, the presence or absence of the 2-2-4 haplotype can be determined following enzymatic amplification using restriction fragment length polymorphism analysis. In another embodiment, following enzymatic amplification, the presence or absence of the 2-2-4 haplotype is determined using sequence analysis.

As used herein, the term "nucleic acid" means a polynucleotide such as deoxyribonucleic acid (DNA) or ribonucleic acid (RNA) and encompasses both single-stranded and double-stranded nucleic acid. Total genomic DNA is a particularly useful nucleic acid with which to practice a method of the invention.

The term "electrophoretic analysis," as used herein in reference to one or more nucleic acid molecules such as amplified fragments, means a process whereby charged molecules are moved through a stationary medium under the influence of an electric field. Electrophoretic migration separates nucleic acid molecules primarily on the basis of their charge, which is in proportion to their size, with smaller molecules migrating more quickly. The term electrophoretic analysis includes analysis using both slab gel electrophoresis, such as agarose or polyacrylamide gel electrophoresis, and capillary electrophoresis. Capillary electrophoretic analysis, which generally occurs inside a small-diameter (50–100-$\mu$m) quartz capillary in the presence of high (kilovolt-level) separating voltages with separation times of a few minutes, can be particularly useful in the methods of the invention. Using capillary electrophoretic analysis, nucleic acids are conveniently detected by UV absorption or fluorescent labeling, and single-base resolution can be obtained on fragments up to several hundred base pairs. Such methods of electrophoretic analysis, and variants thereof, are well known in the art, as described, for example, in Ausubel et al., *Current Protocols in Molecular Biology* Chapter 2 (Supplement 45) John Wiley & Sons, Inc. New York (1999)). Capillary electrophoresis can be particularly useful to separate fragments containing a variable number of tandem repeat locus (VNTR), as disclosed herein for the Notch4 and D6S273 polymorphic loci.

Restriction fragment length polymorphism (RFLP) analysis also can be useful for determining the presence or absence of a particular allele (Jarcho et al. in Dracopoli et al., *Current Protocols in Human Genetics* pages 2.7.1–2.7.5, John Wiley & Sons, New York Innis et al.,(Ed.), *PCR Protocols*, San Diego: Academic Press, Inc. (1990)). As used herein, the term "restriction fragment length polymorphism analysis" means any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site. The use of RFLP analysis to determine the presence of the HSP70-HOM allele 2 using the restriction enzyme Nco I is disclosed herein in Examples II and III.

The term "sequence analysis," as used herein in reference to one or more nucleic acid molecules such as amplified fragments, means any manual or automated process by which the order of nucleotides in a nucleic acid is determined. It is understood that the term sequence analysis encompasses chemical (Maxam-Gilbert) and dideoxy enzymatic (Sanger) sequencing as well as variations thereof. Thus, the term sequence analysis includes capillary array DNA sequencing, which relies on capillary electrophoresis and laser-induced fluorescence detection and can be performed using, for example, the MegaBACE 1000 or ABI 3700. Also encompassed by the term sequence analysis are thermal cycle sequencing (Sears et al., *Biotechniques* 13:626–633 (1992)); solid-phase sequencing (Zimmerman et al., *Methods Mol. Cell Biol.* 3:39–42 (1992) and sequencing with mass spectrometry such as matrix-assisted laser desorption/ionization time-of-flight mass spectrometry MALDI-TOF MS (Fu et al., *Nature Biotech.* 16: 381–384 (1998)). The term sequence analysis also includes, for example, sequencing by hybridization (SBH), which relies on an array of all possible short oligonucleotides to identify a segment of sequences present in an unknown DNA (Chee et al., *Science* 274:61–614 (1996); Drmanac et al., *Science* 260:1649–1652 (1993); and Drmanac et al., *Nature Biotech.* 16:54–58 (1998)). One skilled in the art understands that these and additional variations are encompassed by the term sequence analysis as defined herein. See, in general, Ausubel et al., supra, Chapter 7 and supplement 47.

The invention also provides a method of diagnosing or predicting susceptibility to an autoimmune disease in an individual by determining the presence or absence in the individual of a 2-2-4 haplotype at the Notch4, HSP70-HOM and D6S273 loci, where the method includes the steps of obtaining material containing nucleic acid including Notch4, HSP70-HOM and D6S273 loci from the individual; enzymatically amplifying the nucleic acid to produce a first amplified fragment containing the Notch4 locus; enzymatically amplifying the nucleic acid to produce a second amplified fragment containing the HSP70-HOM locus; and enzymatically amplifying the nucleic acid to produce a third amplified fragment containing the D6S273 locus. One skilled in the art understands that the first, second and third amplified fragment can be obtained simultaneously or in any order, and that no specific limitation is intended by their order of presentation here. Additionally, one skilled in the art understands that the amplified fragments need only include part of the recited locus. Thus, for example, a first amplified fragment need only contain that portion of exon 1 of the Notch4 locus containing the polymorphic CTG site and need not contain, for example, the Notch coding sequence in its entirety.

In another embodiment, a method of the invention further includes the steps of electrophoresing the first amplified fragment, thereby determining whether a Notch4, allele 2 is present; electrophoresing the second amplified fragment, thereby determining whether a HSP70-HOM allele 2 is present; and electrophoresing the third amplified fragment, thereby determining whether a D6S273 allele 4 is present. One skilled in the art understands that the fragments can be electrophoresed simultaneously or sequentially in any order. The presence of the Notch4 allele 2, the HSP70-HOM allele 2 and the D6S273 allele 4 together indicate that the 2-2-4 haplotype is present and therefore diagnoses or predicts susceptibility to an autoimmune disease such as Crohn's disease, rheumatoid arthritis or Type I diabetes. An additional step of restricting the second amplified fragment with Nco I or an isoschizomer thereof can be performed if desired in determining whether HSP70-HOM allele 2 is present. See Example II.

As used herein, the term "material" means any biological matter from which nucleic acid can be prepared. For example, the term material encompasses whole blood, plasma, saliva or other bodily fluid or tissue that contains nucleic acid. A preferred material is whole blood, which can be obtained readily by non-invasive means and used to prepare genomic DNA for enzymatic amplification.

A variety of molecular methods useful for determining the presence or absence of an allele that makes up the 2-2-4 haplotype, or another disease-associated allele as described further below, are well known in the art. One skilled in the art understands that, where the presence or absence of a disease-associated haplotype is to be determined, individual alleles are detected by any combination of molecular methods. See, in general, Birren et al. (Eds.) *Genome Analysis: A Laboratory Manual* Volume 1 (Analyzing DNA) New York, Cold Spring Harbor Laboratory Press (1997).

Allele-specific oligonucleotide hybridization also can be used to detect a disease-associated allele. Allele-specific oligonucleotide hybridization is based on the use of a labeled oligonucleotide probe having a sequence perfectly complementary, for example, to a disease-associated sequence. Under appropriate conditions, the allele-specific probe hybridizes to a nucleic acid containing the disease-associated allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-associated allele by using an allele-specific oligonucleotide primer that is perfectly complementary to the nucleotide sequence of the disease-associated allele but which has one or more mismatches as compared to other alleles (Mullis et al. (Eds.), *The Polymerase Chain Reaction*, Birkhäuser, Boston, (1994)). One skilled in the art understands that the one or more nucleotide mismatches that distinguish between the disease-associated allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that can be used to detect a Notch4 2 allele, a HSP70-HOM 2 allele, a D6S273 4 allele, or to detect a disease-associated allele, according to a method of the invention. HMA is useful for detecting the presence of a polymorphic sequence since a DNA duplex carrying a mismatch has reduced mobility in a polyacrylamide gel compared to the mobility of a perfectly base-paired duplex (Delwart et al., *Science* 262:1257–1261 (1993); White et al., *Genomics* 12:301–306 (1992)).

The technique of single strand conformational polymorphism (SSCP) also can be used to detect the presence or absence of a Notch4 2 allele, a HSP70-HOM 2 allele, a D6S273 4 allele, or to detect the presence or absence of a disease-associated allele (see Hayashi, *PCR Methods Applic.* 1:34–38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also can be used to detect a Notch4 2 allele, HSP70-HOM 2 allele, D6S273 4 allele or disease-associated allele. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other well-known approaches for determining the presence or absence of a Notch4 2 allele, HSP70-HOM 2 allele, D6S273 4 allele or a disease-associated allele include automated sequencing and RNAase mismatch techniques (Winter et al., *Proc. Natl. Acad. Sci.* 82:7575–7579 (1985)). In view of the above, one skilled in the art realizes that the methods of the invention for diagnosing or predicting susceptibility to an autoimmune disease in an individual can be practiced using one of the well known assays described above, or another art-recognized assay for detecting a disease-associated haplotype or allele.

The invention also provides a method of diagnosing or predicting susceptibility to an autoimmune disease in an individual by determining the presence or absence in the individual of a disease-associated haplotype, which is associated with a 2-2-4 haplotype at the Notch4, HSP70-HOM and D6S273 loci, where the presence of the disease-associated haplotype is diagnostic of or predictive of susceptibility to the autoimmune disease. In one embodiment, the disease-associated haplotype is associated with the autoimmune disease with an odds ratio of at least 5 and a lower 95% confidence limit of greater than 1.

In another embodiment of the present invention, methods are provided for diagnosing or predicting susceptibility to an autoimmune disease in an individual by determining the presence or absence of a disease-associated allele associated with the 2-2-4 haplotype at the Notch4, HSP70-HOM and D6S273 loci, where the presence of the disease-associated allele is diagnostic of or predictive of susceptibility to the autoimmune disease. In one embodiment, the disease-associated allele is associated with the autoimmune disease with an odds ratio of at least 5 and a lower 95% confidence limit of greater than 1. The presence or absence of the disease-associated haplotype or allele is determined using any of a variety of routine methods, described herein above.

As used herein, the term "associated with," when used in reference to a disease-associated haplotype or disease-associated allele, and the 2-2-4 haplotype, means that the disease-associated haplotype or disease-associated allele and the 2-2-4 haplotype are inherited together more often than would be expected according to traditional Mendelian genetics. Thus, the presence of such a disease-associated haplotype or disease-associated allele, which is associated with the 2-2-4 haplotype, can be used as a surrogate for the 2-2-4 haplotype to diagnose or predict susceptibility to Crohn's disease, rheumatoid arthritis, type I diabetes mellitus or another autoimmune disease as described herein above.

The present methods are based on the finding that three markers, Notch4, HSP70-HOM, and D6S273, spanning 0.5 Mb within the MHC class III, make up a haplotype that is strongly associated with Crohn's disease. Thus, the 2-2-4 haplotype is a useful diagnostic for Crohn's disease and related autoimmune disorders. Furthermore, based on this finding, it is clear that one or more of the three alleles (Notch4 allele 2, HSP70-HOM allele 2 or D6S273 allele 4) can be substituted with an alternative genetic marker to produce another diagnostic haplotype. Such a haplotype is designated herein as a "disease-associated haplotype" and is characterized, in part, by being associated with the 2-2-4 haplotype. Exemplary genetic markers that can be a disease-associated allele or that can be combined with, or substituted within, the 2-2-4 haplotype to produce a disease-associated haplotype include those shown in Table 1.

TABLE 1

| Net Position | Gene | Note | Type | Position of Sequence | |
|---|---|---|---|---|---|
| | Notch4 | | | | |
| 24,000 | exon 1 | ms | (CTG)n | 24,000 | U89335 |
| 33,420 | intron 12 | ms | (TA)n | 33,420 | U89335 |
| 36,288 | intron 17 | ms | (TTAT)n | 36,288 | U89335 |

TABLE 1-continued

| Net Position | Gene | Note | Type | Position of Sequence | |
|---|---|---|---|---|---|
| | RAGE | | | | |
| 88,458 | intron 8 Tenascin X | ms | | 43,768 | U89336 |
| 169,745 | intron 12 | ms | (TTTC)n | 62,474 | U89337 |
| 180,728 | intron 19 C4B | ms | (TTTC)n | 73,457 | U89337 |
| 222,141 | intron 15 C2 | ms | (GGA)n | 32,500 | AF019413 |
| 274,871 | intron 9 | ms | (CAT)n | 85,230 | AF019413 |
| 281,003 | C2D | | | 91,362 | AF019413 |
| 296,985 | Repeat HSP-HOM | ms | (CGGG)n | 15,595 | AF134726 |
| 383,879 | | | | 102,489 | AF134726 |
| 493,383 | D6S273 | | | 34,073 | AF129756 |

A useful disease-associated haplotype can contain, for example, a RAGE allele such as a polymorphic allele in intron 8 (accession U89336) or a tenasin X allele (Weissensteiner et al., *Eur. J. Immunogen.* 24:201–209 (1997); also, see accession U89337), in combination with one or more of Notch 4 allele 2, HSP70-HOM allele 2 or D6S273 allele 4 (see Table 1). A disease-associated haplotype also can include, if desired, a C2, C4 or other complement allele such as a C4B microsatellite allele in intron 15, a C2 microsatellite allele in intron 9; or a polymorphic "C2D" allele (Sullivan et al., *J. Rheumatol.* 21:1128–1133 (1994); Cross et al., *Exp. Clin. Immunogen.* 7:53–63 (1990); Doherty et al., *Autoimmunity* 18:243–249 (1994) and Lhotta et al., *Diabetes Care* 19:53–55 (1996)). In addition, a disease-associated haplotype can contain, for example, a HSP70-1 allele or HSP70-2 allele, such as an allele at the HSP70-2 Pst I polymorphic site, in combination with one or more of Notch 4 allele 2, HSP70-HOM allele 2 or D6S273 allele 4 (Milner and Campbell, supra, 1992; Pociot et al., *Scand. J. Immunol.* 38:491–495 (1993); Vinasco et al., *Tissue Antigens* 50:71–73 (1997)). A useful disease-associated haplotype also can be a four allele, five allele or larger haplotype that combines Notch 4 allele 2, HSP70-HOM allele 2 and D6S273 allele 4 with one or more additional alleles, for example, a tenascin X allele, C4B allele or C2 allele.

The term "disease-associated allele," as used herein, means a molecular variation that tends to be inherited together with a disease such as Crohn's disease. Any allele from the polymorphic loci shown in Table 1 can be a disease-associated allele of the invention.

A disease-associated allele useful in the invention can be, for example, a single nucleotide polymorphism (snp) or can be a microsatellite (ms) or variable number tandem repeat (VNTR) polymorphism. In addition to nucleotide substitutions, insertions or deletions, one skilled in the art understands that a disease-associated allele also can be a molecular variation such as abnormal methylation or other modification that does not produce a difference in the primary nucleotide sequence of the disease-associated allele as compared to another allele.

In one embodiment, the strength of the association between a disease-associated haplotype or allele and an autoimmune disease such as Crohn's disease is characterized by an odds ratio of at least 5 with a lower 95% confidence interval limit of greater than 1. Such an odds ratio can be, for example, at least 5.5, 6.0, 6.5, 7.0, 7.5 or 8.0 with a lower 95% confidence interval limit of greater than 1, such as an odds ratio of at least 8 with a 95% confidence interval of 1.55 to 100 (see FIG. 3). Methods for determining an odds ratio are well known in the art (see, for example, Schlesselman et al., *Case Control Studies: Design, Conduct and Analysis* Oxford University Press, New York (1982).

In another embodiment, a disease-associated haplotype or allele is associated with an autoimmune disease with a p value of equal to or less than 0.0097. As used herein the term "p value" is synonymous with "probability value." The expected p value for the association between a random haplotype (or allele) and disease is 1.00. A p value of less than 0.05 indicates that haplotype and disease do not appear together by chance but are influenced by positive factors. The statistical threshold for significance of linkage has been set at a level of allele sharing for which false positives would occur once in twenty genome scans (p=0.05). A disease-associated haplotype or disease-associated allele can be associated with an autoimmune disease with, for example, a p value of 0.04, 0.03, 0.02, 0.01, 0.009, 0.008, 0.007, 0.006, 0.005, 0.004, 0.003, 0.002 or 0.001, or with a p value of 0.00095, 0.0009, 0.00085 or 0.0008. It is recognized that, in some cases, p values may need to be corrected, for example, to account for factors such as sample size (number of families), genetic heterogeneity (linked forms and unlinked forms within the particular disease), clinical heterogeneity, or analytical approach (parametric or nonparametric method).

The following examples are intended to illustrate but not limit the present invention.

EXAMPLE I

Selection of Study Subjects

This example demonstrates the selection of appropriate study subjects For the test.

Details of the IBD patient archive at Cedars-Sinai Medical Center have been reported elsewhere and ascertainment of subjects continues (Shanahan et al., *Annu. Rev. Med.* 43:125–33 (1992); Toyoda et al., *Gastroenterol.* 104:741–748 (1993); and Yang et al., *Gut* 34:517–524 (1993)). For this study, the case control panel was composed of 108 patients with CD and 69 ethnically matched controls, mainly spouses. The family panel was composed of 56 families with at least one member affected with CD and no members affected with ulcerative colitis (CD only panel; 196 individuals total). The genotype of any parents For whom DNA was unavailable was determined by genotyping unaffected siblings. The use of human subjects was approved by the Institutional Review Board of Cedars Sinai Medical Center. Diagnosis of CD was determined by standard criteria (Shanahan et al., in Kelley W. (Ed.), *Textbook of Internal Medicine*, 489–502 (1989), and Vasiliauskas et al., *Gastroenterol.* 110:1710–1719 (1996)).

EXAMPLE II

Selection of Markers and Genotyping

This example describes the genetic markers used and genotyping procedures in this study.

The 20 genetic markers used in this study are listed in FIG. 1 along with the location of the marker on the standard MHC map (e.g. Trowsdale et al., supra (1991)); a cartoon showing the relative positions of these markers is at the top of FIG. 3. Microsatellite markers ("ms") were adapted to fluorescence-based high throughput genotyping technology (ABI 373 DNA sequencer, GeneScan® and Genotyper® software) from the references given using the PCR primers indicated in FIG. 1.

PCR was performed using AmpliTaq Gold® following the manufacturer's recommendations (Perkin Elmer, Foster City, Calif.). Primer sequences were adapted from the literature or designed using PCR primer design software (Oligo 5.0) and the DNA sequence listed. D6S273 primers were purchased from and all other primers were synthesized by Research Genetics (Huntsville, Ala.). After PCR, single nucleotide polymorphism ("snp") markers were digested with the indicated restriction enzyme and run on 1.2% agarose gels following standard procedures (Sambrook et al., *Molecular Cloning: A Laboratory Manual* New York, Cold Spring Harbor Press (1989)) configured for high throughput.

Notch4 allele 2 was detected as follows. The $(CTG)_n$ repeat is located in exon 1 of the Notch4 gene, between nucleotides 24,000 and 24,026 of GenBank accession number U89335. Using the primers listed in FIG. 1 (SEQ ID NOS: 9 and 10), allele 2 was detected as the 325 bp allele.

HSP70-HOM contains a polymorphism at nucleotide 2437. This "T" to "C" nucleotide transition corresponds to a methionine to threonine substitution at amino acid 493 (M493T; Milner and Campbell, supra, 1992). The sequence of the HSP genes is available as GenBank accession number AF134726. Using the primers indicated in FIG. 1 (SEQ ID NOS: 11 and 12), the "1" allele yields an uncleaved 1.1 kb fragment with restriction enzyme Nco I (Thr). The "2" allele gives two bands of about 750 bp and 350 bp with this restriction enzyme (Met).

The D6S273 marker is located at nucleotide number 34,073 to 34,114 of GenBank accession number AF129756.1. D6S273 allele 4 was identified using a FAM-labeled primer set purchased from Research Genetics (see SEQ ID NOS: 13 and 14 shown in FIG. 1). Allele "4" was evident as a 133 bp allele.

Association tests on genotypes from the case control panel were performed using SAGE. The TDT was performed using GeneHunter® 2.0 and TDT exact implemented in SAGE.

EXAMPLE III

Association of a Notch4 Allele with Crohn's Disease

This example describes the association of the Notch4 allele 2 with Crohn's disease in an Ashkenazi Jewish population.

Genotyping For the 21 markers listed in FIG. 1 was performed in our case-control panel of 108 CD and 69 control subjects of Ashkenazi Jewish ethnicity. As FIG. 2 shows, a significant negative association between CD and allele 4 of the beta-tubulin (TUBB) locus and a significant positive association between CD and allele 2 of the Notch4 locus were observed (p=0.014 and 0.011, respectively).

High resolution molecular genotyping For the HLA-DR, -DQ, and DP loci in this case control panel has been previously reported (Trachtenberg et al., *Human Immunol.* 55 (Suppl. 1): 59 (1997)) and an association between CD and HLA-DRB1*0103 was observed (24/304 CD subjects compared with 5/232 control subjects, p=0.004). However, since the contribution to this association was observed in non-Jews, rather than Jews (only 3/125 Jewish CD subjects were HLA-DRB1*0103 compared with 0/68 control subjects, p=NS), the observed association between CD and the Notch4 allele 2 is not due to linkage disequilibrium between Notch4 and HLA-DRB1.

These results demonstrate that Notch4 allele 2 is significantly associated with Crohn's disease in an Ashkenazi Jewish population and indicate that this allele can be a useful diagnostic marker.

EXAMPLE IV

Identification of a Three Marker Haplotype Strongly Associated with Crohn's Disease This example describes identification of a three marker haplotype strongly associated with Crohn's disease.

A. Association of the 2-2-4 Haplotype in the Family Panel

Genotyping For 21 MHC markers was performed in the family panel of 56 families with at least 1 proband affected with CD and none with ulcerative colitis (CD only families). As shown in FIG. 3 (line 1), using the TDT, a significant distortion of transmission of allele 2 of the Notch4 locus to CD-affecteds was observed, with allele 2 transmitted to affecteds 31 times and not transmitted 15 times (p=0.011, GeneHunter® 2.0; p=0.030, TDTEx, SAGE). No significant distortion of alleles at the TUBB locus was observed (data not shown). Therefore, the association between CD and Notch4 allele 2 observed in the case control panel was confirmed in the family panel using the TDT.

With the addition of information from the marker adjacent to Notch4, there was significant distortion of the transmission of the two allele Notch4 and HSP70-HOM 2-2 haplotype to affecteds; the 2-2 haplotype was transmitted to affecteds 29 times and not transmitted 11 times (p=0.0044, GeneHunter® 2.0; FIG. 3, lines 2–6). With the addition of the next marker along the MHC, there was a further increase in the significance of the distortion of the transmission: the three allele Notch4/HSP70-HOM/D6S273 2-2-4 haplotype was transmitted to affecteds 16 times and not transmitted 2 times (p=0.00097, GeneHunter® 2.0; FIG. 3, line 7–10). No significant transmission distortion was observed with 4 allele haplotypes using the GeneHunter® 2.0 program.

B. Association of the 2-2-4 Haplotype in the Case Control Panel

To test whether an association between the Notch4/HSP70-HOM/D6S273 2-2-4 haplotype and CD was evident in the case control panel as well as the family panel, the presence of the 2-2-4 haplotype was inferred in the case control subjects by the presence of the combination of the individual markers.

The results show that the association of the 2-2-4 haplotype with Crohn's disease is stronger than the association of the Notch4 allele alone with Crohn's disease.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A method of diagnosing or predicting susceptibility to Crohn's disease in an Ashkenazi Jewish individual, comprising determining the presence or absence in said individual of a 2-2-4 haplotype at the Notch 4, HSP70-HOM and D6S273 loci,
   wherein the presence of said 2-2-4 haplotype is diagnostic of or predictive of susceptibility to Crohn's disease.

2. The method of claim 1, wherein determining the presence or absence of the 2-2-4 haplotype comprises enzymatic amplification of nucleic acid from said individual.

3. The method of claim 2, wherein determining the presence or absence of the 2-2-4 haplotype further comprises electrophoretic analysis.

4. The method of claim 2, wherein determining the presence or absence of the 2-2-4 haplotype further comprises restriction fragment length polymorphism analysis.

5. The method of claim 2, wherein determining the presence or absence of the 2-2-4 haplotype further comprises sequence analysis.

6. The method of claim 1, wherein determining the presence or absence of the 2-2-4 haplotype comprises:
   (a) obtaining material comprising nucleic acid including Notch4, HSP70-HOM and D6S273 loci from said individual;
   (b) enzymatically amplifying said nucleic acid to produce a first amplified fragment comprising said Notch4 locus;
   (c) enzymatically amplifying said nucleic acid to produce a second amplified fragment comprising said HSP70-HOM. locus; and
   (d) enzymatically amplifying said nucleic acid to produce a third amplified fragment comprising said D6S273 locus.

7. The method of claim 6, wherein determining the presence or absence of the 2-2-4 haplotype further comprises:
   (e) electrophoresing said first amplified fragment, thereby determining whether a Notch4 allele 2 is present;
   (f) electrophoresing said second amplified fragment, thereby determining whether a HSP70-HOM allele 2 is present; and
   (g) electrophoresing said third amplified fragment, thereby determining whether a D6S273 allele 4 is present,
   wherein the presence of said Notch4 allele 2, said HSP70-HOM allele 2 and said D6S273 allele 4 indicates that said 2-2-4 haplotype is present.

8. The method of claim 6, wherein step (c) further comprises restricting said second amplified fragment with Nco I or an isoschizomer thereof.

* * * * *

SEQUENCE LISTING

```
<160> NUMBER OF SEQ ID NOS: 40

<210> SEQ ID NO 1
<211> LENGTH: 23
<212> TYPE: DNA
<213> ORGANISM: Homo sapiens

<400> SEQUENCE: 1
ctgtaatccc agctactcaa tcg                                           23

<210> SEQ ID NO 2
<211> LENGTH: 24
<212> TYPE: DNA
<213> ORGANISM: Homo sapiens

<400> SEQUENCE: 2
gggagactta aacagcagaa atgt                                          24

<210> SEQ ID NO 3
<211> LENGTH: 21
<212> TYPE: DNA
<213> ORGANISM: Homo sapiens

<400> SEQUENCE: 3
tcgggatcat ttcagtaatc t                                             21

<210> SEQ ID NO 4
<211> LENGTH: 18
<212> TYPE: DNA
<213> ORGANISM: Homo sapiens
```

-continued

```
<400> SEQUENCE: 4
gggatccgct gtaactct                                                18

<210> SEQ ID NO 5
<211> LENGTH: 22
<212> TYPE: DNA
<213> ORGANISM: Homo sapiens

<400> SEQUENCE: 5
ggacaatatt ttgctcctga gg                                           22

<210> SEQ ID NO 6
<211> LENGTH: 18
<212> TYPE: DNA
<213> ORGANISM: Homo sapiens

<400> SEQUENCE: 6
gctttgatct cccccctc                                                18

<210> SEQ ID NO 7
<211> LENGTH: 24
<212> TYPE: DNA
<213> ORGANISM: Homo sapiens

<400> SEQUENCE: 7
gagctcggga gtgaggcaga acag                                         24

<210> SEQ ID NO 8
<211> LENGTH: 24
<212> TYPE: DNA
<213> ORGANISM: Homo sapiens

<400> SEQUENCE: 8
tgaggtgtgt tcattagtca actc                                         24

<210> SEQ ID NO 9
<211> LENGTH: 21
<212> TYPE: DNA
<213> ORGANISM: Homo sapiens

<400> SEQUENCE: 9
cgtctctatt tgggcagtga g                                            21

<210> SEQ ID NO 10
<211> LENGTH: 18
<212> TYPE: DNA
<213> ORGANISM: Homo sapiens

<400> SEQUENCE: 10
ggccgaggag gaagaaga                                                18

<210> SEQ ID NO 11
<211> LENGTH: 26
<212> TYPE: DNA
<213> ORGANISM: Homo sapiens

<400> SEQUENCE: 11
ccggatccca taggcctcag agaacc                                       26

<210> SEQ ID NO 12
<211> LENGTH: 21
<212> TYPE: DNA
<213> ORGANISM: Homo sapiens
```

<400> SEQUENCE: 12
gtaacttaga ttcaggtctg g                                    21

<210> SEQ ID NO 13
<211> LENGTH: 20
<212> TYPE: DNA
<213> ORGANISM: Homo sapiens

<400> SEQUENCE: 13
accaaacttc aaattttcgg                                      20

<210> SEQ ID NO 14
<211> LENGTH: 20
<212> TYPE: DNA
<213> ORGANISM: Homo sapiens

<400> SEQUENCE: 14
gcaacttttc tgtcaatcca                                      20

<210> SEQ ID NO 15
<211> LENGTH: 20
<212> TYPE: DNA
<213> ORGANISM: Homo sapiens

<400> SEQUENCE: 15
ggagctaaaa gttctaactc                                      20

<210> SEQ ID NO 16
<211> LENGTH: 20
<212> TYPE: DNA
<213> ORGANISM: Homo sapiens

<400> SEQUENCE: 16
tgtctcaaaa tattaatgtg                                      20

<210> SEQ ID NO 17
<211> LENGTH: 24
<212> TYPE: DNA
<213> ORGANISM: Homo sapiens

<400> SEQUENCE: 17
tagtaatttg ttgggtgaat gaca                                 24

<210> SEQ ID NO 18
<211> LENGTH: 20
<212> TYPE: DNA
<213> ORGANISM: Homo sapiens

<400> SEQUENCE: 18
cacactgcca ctcctcagat                                      20

<210> SEQ ID NO 19
<211> LENGTH: 24
<212> TYPE: DNA
<213> ORGANISM: Homo sapiens

<400> SEQUENCE: 19
catagtggga ctctgtctcc aaag                                 24

<210> SEQ ID NO 20
<211> LENGTH: 24
<212> TYPE: DNA

-continued

```
<213> ORGANISM: Homo sapiens

<400> SEQUENCE: 20
agatccttcc ctgtgagttc tgct                                          24

<210> SEQ ID NO 21
<211> LENGTH: 22
<212> TYPE: DNA
<213> ORGANISM: Homo sapiens

<400> SEQUENCE: 21
gtgcctggtt ctggagcctc tc                                            22

<210> SEQ ID NO 22
<211> LENGTH: 24
<212> TYPE: DNA
<213> ORGANISM: Homo sapiens

<400> SEQUENCE: 22
tgagacagag gataggagag acag                                          24

<210> SEQ ID NO 23
<211> LENGTH: 24
<212> TYPE: DNA
<213> ORGANISM: Homo sapiens

<400> SEQUENCE: 23
ggtttctctg actgcatctt gtcc                                          24

<210> SEQ ID NO 24
<211> LENGTH: 23
<212> TYPE: DNA
<213> ORGANISM: Homo sapiens

<400> SEQUENCE: 24
tcatggggag aacctgcaga gaa                                           23

<210> SEQ ID NO 25
<211> LENGTH: 22
<212> TYPE: DNA
<213> ORGANISM: Homo sapiens

<400> SEQUENCE: 25
cctctctccc ctgcaacaca ca                                            22

<210> SEQ ID NO 26
<211> LENGTH: 24
<212> TYPE: DNA
<213> ORGANISM: Homo sapiens

<400> SEQUENCE: 26
gcctctagat ttcatccagc caca                                          24

<210> SEQ ID NO 27
<211> LENGTH: 22
<212> TYPE: DNA
<213> ORGANISM: Homo sapiens

<400> SEQUENCE: 27
gtgtgtgttg cagggagag ag                                             22

<210> SEQ ID NO 28
<211> LENGTH: 22
```

```
<212> TYPE: DNA
<213> ORGANISM: Homo sapiens

<400> SEQUENCE: 28
gcactccagc ctaggccaca ga                                              22

<210> SEQ ID NO 29
<211> LENGTH: 21
<212> TYPE: DNA
<213> ORGANISM: Homo sapiens

<400> SEQUENCE: 29
acaatggaca cttgggttac t                                               21

<210> SEQ ID NO 30
<211> LENGTH: 19
<212> TYPE: DNA
<213> ORGANISM: Homo sapiens

<400> SEQUENCE: 30
aatgagatgc cacctgaaa                                                  19

<210> SEQ ID NO 31
<211> LENGTH: 24
<212> TYPE: DNA
<213> ORGANISM: Homo sapiens

<400> SEQUENCE: 31
ttatctactt atagtctatc acgg                                            24

<210> SEQ ID NO 32
<211> LENGTH: 24
<212> TYPE: DNA
<213> ORGANISM: Homo sapiens

<400> SEQUENCE: 32
ggcttgactt gaaactcaga gacc                                            24

<210> SEQ ID NO 33
<211> LENGTH: 25
<212> TYPE: DNA
<213> ORGANISM: Homo sapiens

<400> SEQUENCE: 33
gatcgctcac cagcacactg gctat                                           25

<210> SEQ ID NO 34
<211> LENGTH: 25
<212> TYPE: DNA
<213> ORGANISM: Homo sapiens

<400> SEQUENCE: 34
ctgggcaaca gagcgagctc cgtct                                           25

<210> SEQ ID NO 35
<211> LENGTH: 22
<212> TYPE: DNA
<213> ORGANISM: Homo sapiens

<400> SEQUENCE: 35
tccttacagc agagatatgt gg                                              22

<210> SEQ ID NO 36
```

-continued

```
<211> LENGTH: 22
<212> TYPE: DNA
<213> ORGANISM: Homo sapiens

<400> SEQUENCE: 36
agatggcatt tggagagtgc ag                                             22

<210> SEQ ID NO 37
<211> LENGTH: 21
<212> TYPE: DNA
<213> ORGANISM: Homo sapiens

<400> SEQUENCE: 37
caacacactg atttccatag c                                              21

<210> SEQ ID NO 38
<211> LENGTH: 21
<212> TYPE: DNA
<213> ORGANISM: Homo sapiens

<400> SEQUENCE: 38
aatgggctac tacttcacac c                                              21

<210> SEQ ID NO 39
<211> LENGTH: 21
<212> TYPE: DNA
<213> ORGANISM: Homo sapiens

<400> SEQUENCE: 39
gaaatgtgag aataaaggag a                                              21

<210> SEQ ID NO 40
<211> LENGTH: 20
<212> TYPE: DNA
<213> ORGANISM: Homo sapiens

<400> SEQUENCE: 40
gataaagggg aactactaca                                                20
```